United States Patent [19]

Jederström et al.

[11] Patent Number: 4,997,867

[45] Date of Patent: Mar. 5, 1991

[54] STABLE COMPOSITIONS

[75] Inventors: Gustaf L. Jederström, Upplands-Väsby, Sweden; John J. Sciarra, Locust Valley, N.Y.

[73] Assignee: Pharmacia AB, Uppsala, Sweden

[21] Appl. No.: 247,380

[22] Filed: Sep. 21, 1988

Related U.S. Application Data

[63] Continuation of Ser. No. 165,463, Mar. 8, 1988, abandoned, which is a continuation of Ser. No. 865,824, May 22, 1986, abandoned.

[30] Foreign Application Priority Data

May 23, 1985 [SE] Sweden ................................ 8502553

[51] Int. Cl.$^5$ .......................... C08L 3/00; C08L 1/00; C08K 5/07
[52] U.S. Cl. ........................................ 524/47; 524/54; 524/732; 524/733; 524/734; 527/300; 527/311; 527/312; 527/313
[58] Field of Search ...................... 524/47, 54, 55, 732, 524/733, 734; 525/54.2, 54.24, 54.26, 54.3, 54.31; 527/300, 311, 312, 313

[56] References Cited

U.S. PATENT DOCUMENTS 4,410,571 10/1983 Korpman ............................ 524/386
4,587,308 5/1986 Makita et al. ...................... 525/373

*Primary Examiner*—Nathan M. Nutter
*Attorney, Agent, or Firm*—Fred Philpitt

[57] ABSTRACT

A method of stabilizing an aqueous dispersion of water-absorbent particles and at least one matrix-forming hydrophilic thickening agent comprises the steps of evacuating gas from said dispersion and subjecting the latter to compression by means of a relative pressure sufficient to irreversibly transform the dispersion into a stable particle-matrix system. A method of preparing a stable semi-solid preparation of dry, preferably bead-shaped water-absorbent particles comprises forming a homogenous dispersion comprising from 30 to 70% by weight of said beads, from 0.1% by weight of at least one hydrophilic thickening agent, capable of forming a matrix for said beads, and from 20 to 55% by weight of water, and stabilizing the dispersion formed as above. The water-absorbent particles may consist of cross-linked carbohydrates or polyacrylamide or derivatives thereof. The stable preparation may advantageously be packed in aerosol type containers and be used for the treatment of wounds and skin.

32 Claims, 1 Drawing Sheet

STABLE COMPOSITIONS

This is a continuation of application Ser. No. 165,463, filed Mar. 8, 1988, and now abandoned which application is a continuation of application Ser. No. 865,824 filed May 22, 1986, and now abandoned.

TECHNICAL FIELD

The present invention relates to a method of stabilizing an aqueous dispersion containing water-absorbent particles, to a method for preparing a stable semi-solid preparation containing such particles, e.g. small water-absorbent beads of cross-linked hydrophilic polymers, such as cross-linked dextran, and to stable preparations prepared by such a method.

BACKGROUND OF THE INVENTION

Small dry water-absorbent beads of cross-linked dextran and similar cross-linked carbohydrates, such as cross-linked starch, cross-linked cellulose, cross-linked agarose, etc. have found extensive commercial use as excellent agents for topical treatment of discharging wounds, such as burn wounds, leg ulcers, bed wounds, etc. See e.g. GB Pat. No. 1,454,055, which is incorporated herein by reference.

The beads are usually applied on the wounds in the form of the dry beads as such (a "powder-like" preparation), or as an ointment or paste formed by simply mixing the beads with glycerol, low molecular polyethylene glycols having an average molecular weight of 400-600, or similar carriers. These preparations have certain drawbacks. For example, the powder-like preparation has the disadvantage that it is difficult to handle and apply, because of its powdery form. The paste preparation represents an improvement of the "powder-like" preparation in that it is more coherent and more convenient to apply to a wound. However, the prior art paste preparations have a tendency to disintegrate on manufacture, storage and use (phase separation), and problems have also been encountered as to the water-absorbent properties of the dry beads.

OBJECTS OF THE INVENTION

There is thus a need for improved physical preparations (galenic forms) of the above mentioned dry beads, which preparations are convenient to handle and apply, which do not easily separate or disintegrate in manufacture, storage or use, and which also retain the valuable properties of the dry beads substantially intact. It is a primary object of the invention to provide a novel preparation of water-absorbent beads of cross-linked hydrophilic polymers, as defined above and in the following, which preparation has these and related advantageous properties. These and other objects of the invention will appear from the following description of the invention and preferred embodiments thereof.

SUMMARY OF THE INVENTION

In a first aspect the invention relates to a method of stabilizing an aqueous dispersion comprising water-absorbent particles and at least one matrix-forming hydrophilic thickening agent, which method comprises the steps of evacuating gas from said dispersion and subjecting the same to a relative pressure sufficient to irreversibly transform the dispersion into a stable, gel-like particle-matrix system (a "hydrogel").

In another aspect the invention relates to a method of preparing a stable semi-solid preparation of small water-absorbent particles, which method comprises the steps of
(a) forming a homogenous dispersion comprising
  (i) from 30 to 70% by weight of said particles,
  (ii) from 0.1% by weight of at least one hydrophilic thickening agent capable of forming a matrix for said particles, and
  (iii) from 20 to 55% by weight of water, and
(b) evacuating gas contained in said dispersion and subjecting the same to compression by means of a relative pressure sufficient to substantially irreversibly transform the dispersion into a stable particle-matrix system.

In a further aspect the invention relates to novel semi-solid preparations or compositions of small water-absorbent particles, which preparations or compositions are characterized by having been made by the above method. In particular, such compositions are provided in the form of a closed aerosol-type container, wherein said pressure is provided by a liquefied propellant and said evacuation of gas is achieved by discharging said gas through the outlet orifice of said container.

In the present context the term "stable" primarily means that the preparation substantially retains its coherency and water-absorbing capacity and is not subjected to phase separation on extended storage.

DESCRIPTION OF PREFERRED EMBODIMENTS

Figure 1:
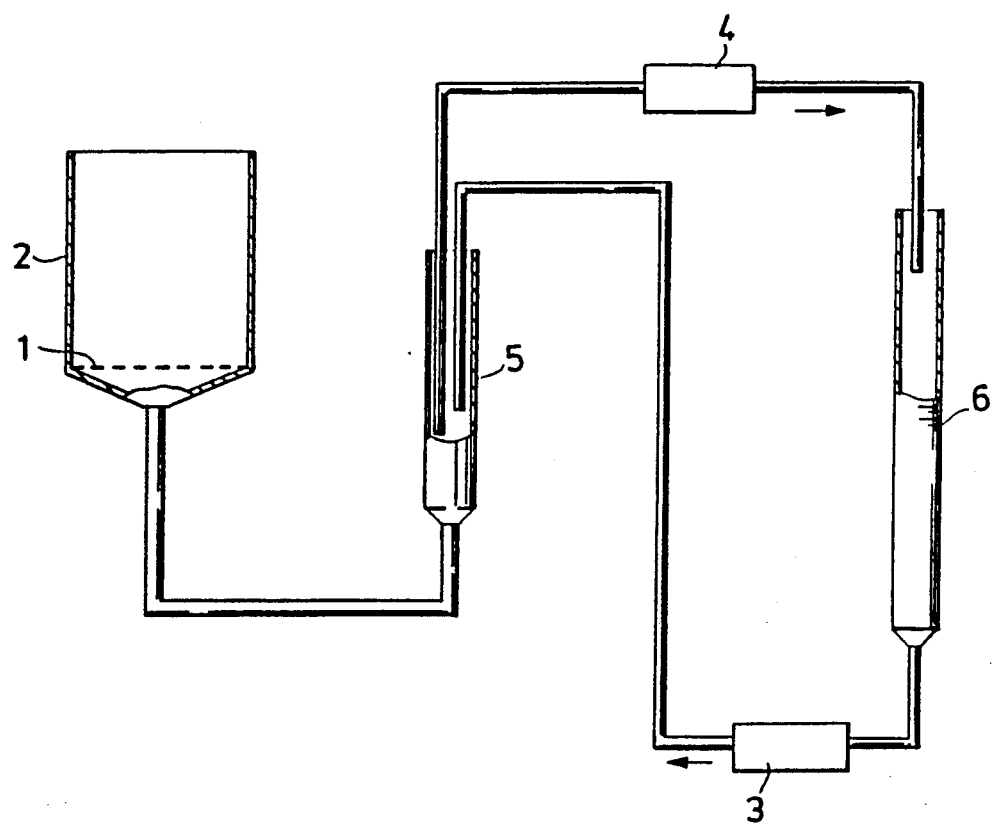

Some presently preferred embodiments of the invention will now be described for the different aspects of the invention conjointly.

In one embodiment of the invention the matrix-forming thickening agent consists of or comprises a poly-lower alkylene glycol having an average molecular weight in the interval from 1500 to 20,000, preferably from 4000 to 10,000, in particular from 6000 to 8000. The preferred polyalkylene glycol is polyethylene glycol.

When the poly-lower alkylene glycol is the only or the major thickening agent, it should be present in a concentration from 2.5 to 15% by weight, based on the total dispersion. Especially when polyethylene glycol is used, the concentration thereof is preferably from 5 to 12% by weight, especially 6 to 10% by weight.

In another embodiment of the invention the thickening agent comprises said poly-lower alkylene glycol in combination with a high molecular, preferably two-dimensional synthetic polymer which is soluble or swellable in water (gel-forming) and is capable of forming a matrix with said beads together with said poly-lower alkylene glycol. Such synthetic polymers are preferably built-up from polycarboxy vinyl chains, polycarboxymethylene chains, poly(ethylene oxide) chains, or chains of hydroxy-lower alkyl, especially hydroxyethyl chains on cellulose polymers. Such polymers preferably have an average molecular weight of from about 400,000, up to about 6,000,000, or even higher. Examples of suitable polymers are i.a. poly(ethylene oxides) such as Polyox ® Coagulant (also called PEG 115M) available from Union Carbide Corp., Danbury, CT, USA, Carbopol 910 (a carboxyvinyl polymer having an average molecular weight of about 500,000, available from B. F. Goodrich Chemical Co., Cleveland, Ohio, USA), Natrosol (a cellulose-hydroxyethyl ether having an average molecular weight of about $1 \times 10^6$ or $2 \times 10^6$, available from Hercules, Wilmington, Delaware, USA), and the like.

In an alternative embodiment the thickening agent comprises a natural gum such as tragacanth, acacia, gum arabicum or the like. This natural gum-type of thickening agent is preferably present in an amount from about 0.1 to about 5% by weight, especially from 0.5 to 3% by weight.

In accordance with the invention it is preferred to also include a low-molecular hydrophilic softening or water-retaining agent. Preferred such agents are low molecular poly-lower alkylene glycols, such as polyethylene glycol, sugar alcohols, such as sorbitol, or the like. Polyethylene glycols having an average molecular weight from about 200 to about 600 are especially preferred, in particular when a natural gum is the only or the major thickening agent. The softening and/or water-retaining agents are usually present in an amount up to about 30% by weight of the total composition, depending on the nature of the thickening agents. When natural gums are used as the thickening agent, the amount of softener is preferably in the range from about 15 to about 25% by weight of the total composition. In other cases the amount of softener is preferably from about 3 to 12% by weight.

The water-absorbent particles used according to the invention are preferably small spherical beads of water-swellable cross-linked polysaccharides such as the particles described in the above-mentioned GB Pat. No. 1,454,055. Said beads preferably have a particle size distribution such that at least about 99% of the particles are within the range from about 50 to 500 microns ($\mu$m), especially from about 100 to 300 $\mu$m. The water-absorbent particles should be present in a concentration from 30 to 70% by weight of the total composition, preferably 40 to 60% by weight, especially 45 to 55% by weight. The particles are preferably chosen so that the finished stable composition will have a water-binding capacity of from 0.9 to 6.0, especially from 2.0 to 3.5 ml water per gram of the composition, as determined by the procedure to be described below with reference to FIG. 1.

It is to be noted that the compositions according to the invention maintain a high degree of water-absorption. This was unexpected since the compositions already contain a high proportion of water. The composition also is capable of causing a continuous flow of a liquid phase for transportion of solid matter, as described in the above mentioned GB Pat. No. 1,454,055, throughout the preparation. Another interesting feature of the invention is that the water absorption profile can be "tailor-made" by varying e.g. the amount of the thickening agent.

As indicated above the gas evacuation and compression steps are critical features for achieving the substantially irreversible transformation of the formed dispersion into the stable semi-solid preparations provided by the invention. The gas evacuation and the compression steps can be carried out either substantially simultaneously or in separate steps.

In a preferred embodiment the dispersion is placed in the bag of an aerosol-type pressure container, in which a liquefied propellant (such as fluorocarbons or hydrocarbons) or an inert pressurized gas is located in the space between the bag and the container wall. The dispersion-containing bag is connected to a discharge valve for expelling the dispersion from the container. Such aerosol containers are known per se and will therefore not be described in any detail. When practicing the invention using such a pressure container the gas evacuation and compression steps are carried out more or less at the same time. When opening said valve gas entrapped in the bag and in the dispersion is thus expelled through the valve (evacuation) before the (compressed) dispersion is discharged through the valve. The relative pressure acting on the dispersion may vary. However, said pressure is preferably from 0.5 to 7.0 kp/cm$^2$ (7 to 100 psig) or even higher, preferably from 3.7 to 6.7 kp/cm$^2$ (53 to 96 psig).

In an alternative embodiment the gas evacuation can be obtained by using negative pressure, i.e. by applying a vacuum to the dispersion to suck-off at least a major part of the entrapped gas (air). A pressure is then applied in order to subject the dispersion to a relative pressure sufficient for causing said substantially irreversible transformation. Said relative pressure is preferably of the same order of magnitude as that indicated above.

The stable preparation according to the invention can be prepared in a dispensing unit (such as the above mentioned pressurized container) for direct use. Alternatively, it can be transferred into a daughter unit for subsequent use, such as an ointment tube. For the preparation to remain stable over long periods of time the dispensing unit should be air-tight.

The stable preparation according to the invention is primarily, but not exclusively intended for medical and cosmetic use, in particular for topical use, e.g. for the treatment of wounds or skin. In addition to the above mentioned ingredients it may also comprise other additives, especially dermatologically acceptable additives, which are known per se in topical compositions. It may also contain, or serve as a carrier for, a variety of cosmetically or therapeutically active substances, such as peptides, enzymes, antibiotics, hormones, macrophages stimulators, corticoids, fungicids, antibacterial agents, antiinflammatory agents, etc., or the particles themselves may have active substances, such as iodione, incorporated therein—see e.g. GB-A-1,514,324. The preparation can also be used in industrial or laboratory processes for separating liquids or particulate materials.

The invention will be further illustrated by the following illustrative—but non-limiting—examples.

EXAMPLES 1 to 21

The ingredients listed in Table 1 below were used for preparing stable semi-solid sprays of dry water-absorbent beads in accordance with the invention, using the following general procedure (with specific reference to Example 14).

(a) Preparation of the dispersion

The high molecular polymer (Polyox® Coagulant, thickening agent) is dispersed in the water and heated (to 90°–95° C). The softener (PEG 400), possible other thickening agents (PEG 8000) and possible other additives are added. The mixture is stirred until it is homogenous and then cooled to room temperature (a clear mixture is usually obtained). This mixture (45% by weight) is then combined with the beads (55% by weight) and stirred to form a homogenous dispersion.

(b) Evacuation and Compression steps

An aerosol-type can system (Sepro®-can available from Continental Can Co., Stamford, USA) or Alu Compack® available from Aerosol-Service AG, Möhlin, Switzerland) is used, comprising a pressure can and an air-tight flexible bag placed in the can. The dispersion from step (a) (200 g) is filled into the bag, and difluoro-dichloromethane propellant (20 g) is filled into the leak-tight interspace between the can and the bag, excerting on the bag a pressure of 67.6 psig (5.80 kg/cm$^2$) at 20° C., which is sufficient for transferring the dispersion into a bead-matrix system. The excess of entrapped air in the filled internal bag is discharged by opening the dispensing valve. Thereafter desired portions of the formed stable semi-solid bead preparation can be dispensed repeatedly until only a small proportion of the preparation remains.

(c) Determining the water-absorbing capacity

The water-absorbing capacity of the prepared products were determined by the following procedure using the apparatus illustrated in FIG. 1.

The sample is resting on a nylon net 1 with a pore size of 10 μm and an area of 3 cm$^2$. The nylon net is glued to a perspex tube 2, which is firmly held together with a glass tube by means of O-rings (not shown). The pressure at the nylon net 1 is kept constant by means of a 2-channel pump 3, 4. One channel 3 fills the burette 5 from the bottom of a graduated pipette 6. Excess of liquid is transported back to the pipette 6 through the other channel 4, which works at a higher rate than the first channel 3. When the absorption causes the surface to sink in the burette 5, air instead of liquid is transported to the pipette. Thus the absorbed volume is the same as the missing volume in the pipette.

The values reported in the following represent the readings after 2 hours absorption in the apparatus, expressed as milliliters of water absorbed per gram of the preparation.

(d) Degree of emptying

This is a measure of how efficiently the preparation can be discharged from the spray container. It was determined by discharging the preparation from the can until no additional amount could be practically dispensed. The weight of residual product was determined, and the degree of emptying (percent by weight) was calculated by the formula $$100 \times \frac{\text{(total weight − residual weight)}}{\text{total weight}}$$

| Ex. No. | Beads | % | Thickening agent | | | | | | Softener | % | Water % | Absorption capacity ml/g | Degree of emptying % |
|---|---|---|---|---|---|---|---|---|---|---|---|---|---|
| | | | Polyethylene Glycol[e] | % | Natural Gum | % | High molecular polymer | % | | | | | |
| 1 | SxG-50C[a] | 55 | 1500 | 5 | | | | | | | 40 | 3.2 | 77 |
| 2 | SxG-50C[a] | 55 | 1500 | 10 | | | | | | | 35 | 2.8 | 71 |
| 3 | SxG-50C[a] | 55 | 8000 | 2.5 | | | | | | | 43.5 | 3.3 | 87 |
| 4 | SxG-50C[a] | 55 | 8000 | 6.5 | | | | | | | 38.5 | 2.4 | 91 |
| 5 | SxG-50C[a] | 55 | 8000 | 11.25 | | | | | | | 33.75 | 2.0 | 91 |
| 6 | SxG-50C[a] | 55 | 8000 | 14 | | | | | | | 31 | 1.2 | 89 |
| 7 | SxG-50C[a] | 55 | 20000 | 6.5 | | | | | | | 38.5 | 3.0 | 95 |
| 8 | SxG-50C[a] | 45 | 8000 | 13.75 | | | | | | | 41.25 | 1.8 | 88 |
| 9 | SxG-50C[a] | 45 | 8000 | 4.4 | | | | | | | 50.6 | 2.7 | 88 |
| 10 | SxG-50C[a] | 50 | 8000 | 7 | | | | | PEG 400 | 10 | 33 | 1.3 | 89 |
| 11 | SxG-50C[a] | 50 | 8000 | 6.5 | | | | | Sorbitol | 5 | 38.5 | 2.5 | 90 |
| 12 | SxG-50C[a] | 55 | 8000 | 3.6 | | | Polyox ® Coagulant[g] | 0.09 | PEG 400 | 10 | 31.3 | 3.3 | 88 |
| 13 | SxG-50C[a] | 50 | 8000 | 7 | | | Polyox ® Coagulant[g] | 0.1 | PEG 400 | 10 | 32.9 | 1.2 | 89 |
| 14[h] | SxG-50C[a] | 55 | 8000 | 6.8 | | | Polyox ® Coagulant[g] | 0.045 | PEG 400 | 4.5 | 33.8 | 3.0 | 91 |
| 15 | SxG-25C[b] | 65 | 8000 | 4.6 | | | Polyox ® Coagulant[g] | 0.08 | PEG 400 | 3 | 27.5 | 2.2 | 97 |
| 16 | Polyacrylamide[c] | 55 | 8000 | 6.5 | | | | | | | 38.5 | 2.0 | 74 |
| 17 | Starch[d] | 55 | 8000 | 6.5 | | | | | | | 38.5 | 0.9 | 86 |
| 18 | SxG-50C[a] | 45 | | | Tragacanth[f] | 0.55 | | | PEG 200 | 27 | 27.5 | 1.9 | 84 |
| 19 | SxG-50C[a] | 45 | | | Tragacanth[f] | 1.5 | | | PEG 300 | 20 | 33.5 | 2.8 | 82 |

[h]properties uneffected by sterilization by gamma radiation (3.2 Mrad)

MATERIALS

The materials used in the Examples are as follows:
(a) Sx G-50C = Sephadex ® G50 Coarse, a cross-linked dextran available from Pharmacia AB, Uppsala, Sweden.
(b) Sx G-25C = Sephadex ® G25 Coarse, cross-linked swelling dextran available from Pharmacia AB, Uppsala, Sweden, having a lower degree of swelling than Sx G-50C.
(c) Polyacrylamide = Bio-Gel P10 from Bio-Rad Laboratories, Richmont, Calif., USA (obtained by co-polymerisation of acrylamide and N,N'-methylene-bis-acrylamide, hydrated diameter 150–300 μm, dry diameter 50–100 μm).
(d) Starch = cross-linked native starch.
(e) PEG 200, 300, 400, 1500, 8000 and 20000, from Farbwerke Hoechst AG, West Germany, the number indicating the average molecular weight of the respective polyethylene glycol.
(f) Tragacanth Laboratory grade, from Fisher Chemicals, USA.
(g) Polyox ® Coagulant (also identified as PEG 115M), poly(ethylene oxide) H(OCH$_2$—CH$_2$)$_n$OH, wherein n ~ 114,000, from Union Carbide Corp., USA.

EXAMPLE 22

The composition prepared and pressurized according to Example 15 was discharged from the spray system and filled into seven aluminum tubes and one glass container, which were then air-tightly sealed. The tubes were stored at 8° C. and 24° C. for 10 and 30 days. The water absorption capacity was determined at the top, at the middle and at the bottom of the tubes. No great differences were found in the values obtained, and the cosmetic properties remained unchanged. This shows that a semi-solid preparation prepared as described can be transferred into a daughter unit such as a wide-mouthed ointment jar or into a collapsible tube, as long as it is contained in an air-tight system.

EXAMPLE 23

A granulate was prepared by mixing Sephadex® G50 coarse (a) (55% w/w) with the following mixture (45% w/w).

|  | % w/w |
|---|---|
| Polyox ® Coagulant$^g$ | 0.2 |
| Polyethylene glycol 8000$^e$ | 8.0 |
| Polyethylene glycol 400$^e$ | 22.2 |
| Dist. water | 89.6 |

The granulate, prepared in a vessel equipped for evacuation of gas and for application of pressure, was then evacuated, and a mechanical pressure was applied. The resulting granulate had been irreversibly transferred into a gel-matrix system. This procedure was repeated, except that no evacuation step was used. When the mechanical pressure was taken away the gel returned to its original granulate consistency.

The semi-solid system was filled into collapsible airtight aluminum tubes. The water-absorbing capacity of this preparation and its cosmetic properties remained unchanged after long-term storage in the air-tight collapsible tubes.

The absorption capacity of the hydrogel was determined at the top and at the bottom of the tubes after 0 and 34 days. The tubes were stored at 30° C. and 50° C. The water-absorption capacity of the dispensed preparation was as follows.

| Aluminum tube No. | | 1 30° C. | | 1 50° C. | |
|---|---|---|---|---|---|
| Storage time | | 0 day | 34 days | 0 day | 34 days |
| Water absorption capacity (ml/g after 60 minutes) | Top | 3.11 | 3.85 | 3.11 | 3.14 |
| | Bottom | 3.17 | 3.92 | 3.17 | 3.39 |

COMPARATIVE EXAMPLE

Example 4 was repeated using a low molecular polyethylene glycol (PEG 1000) instead of PEG 8000. The dispersion did not form any coherent product, and it could not be dispensed from the aerosol can.

What is claimed is:

1. A method of stabilizing an aqueous dispersion comprising
   (i) from about 30 to 70% by weight of water-absorbent particles,
   (ii) from about 20 to 55% by weight of water, and
   (iii) from 0.1% by weight of at least one hydrophilic thickening agent selected from the group consisting of natural gums and polyalkyleneglycols having an average molecular weight of at least 1500,
said method comprising the step of subjecting said dispersion to compression by means of a relative pressure sufficient to substantially irreversibly transform said dispersion into a stable particle-matrix system, said relative pressure being from about 0.5 to 7 kp/cm² (7 to 100 psig).

2. The method of claim 1 wherein said water absorbent particles have a particle size from about 50 to 500 μm.

3. The method of claim 2 wherein said particles are bead-shaped.

4. The method of claim 2 wherein said water-absorbent particles are selected from the group consisting of cross-linked carbohydrates and polyacrylamides.

5. The method of claim 3 wherein said water-absorbent particles are selected from the group consisting of cross-linked carbohydrates and polyacrylamides.

6. The method of claim 1 wherein said hydrophilic thickening agent comprises a poly-lower alkylene glycol having an average molecular weight from 1500-20,000, which is present in an amount of from 2.5 to 15% by weight, based on the total dispersion.

7. The method of claim 6 wherein said thickening agent further comprises a high molecular weight gel forming polymer, which is soluble or swellable in water and is capable of forming a matrix together with said particles and said polyalkylene glycol.

8. The method of claim 7 wherein said gel-forming polymer is a synthetic polymer built-up from polycarboxy vinyl chains, polycarboxylalkylene chains, poly-(alkylene oxide) chains or chains of hydroxyalkyl ether on cellulose polymers, said polymer preferably having a molecular weight of at least 400,000 and being present in an amount up to about 4% by weight of said dispersion.

9. The method of claim 1 wherein said thickening agent comprises a gel-forming natural gum which is present in an amount of up to about 5% by weight of the dispersion.

10. The method of claim 1 wherein said dispersion further comprises a low molecular hydrophilic softening agent in an amount up to about 30% by weight.

11. The method of claim 10 wherein the thickening agent is a natural gum and wherein said low molecular hydrophilic softening agent is present in an amount of from 15 to 25% by weight.

12. The method of claim 1 wherein said dispersion is placed in a closed aerosol-type container, said pressure being applied by a liquified propellant and said evacuation of gas being achieved by discharging the same through an orifice provided in the container, by the action of said propellant.

13. The method of claim 1 comprising the steps of evacuating gas from the dispersion, and subjecting the evacuated dispersion to a hydrostatic pressure.

14. A method of preparing a stable semi-solid preparation of dry water-absorbent particles comprising the steps of
   (a) forming a homogenous dispersion comprising
      (i) from about 30 to 70% by weight of said particles,
      (ii) from 0.1% by weight of at least one hydrophilic thickening agent selected from the group consisting of natural gums and polyalkylene-glycols having an average molecular weight of at least 1500, and capable of forming a matrix for said particles, and
      (iii) from about 20 to 55% by weight of water and
   (b) evacuating gas contained in said dispersion and subjecting said dispersion to compression by means of a relative pressure sufficient to substantially irreversibly transform the dispersion into a stable particle-matrix system, said relative pressure being from about 0.5 to 7 kg/cm² (7 to 100 psig).

15. The method of claim 14 wherein said water absorbent particles have a particle size from about 50 to 500 μm.

16. The method of claim 15 wherein said particles are bead-shaped.

17. The method of claim 16 wherein said water-absorbent particles are selected from the group consisting of cross-linked carbohydrates and polyacrylamides.

18. The method of claim 16 wherein said water-absorbent particles are selected from the group consisting of cross-linked carbohydrates and polyacrylamides.

19. The method of claim 14 wherein said hydrophilic thickening agent comprises a poly-lower alkylene glycol having an average molecular weight from 1500–20,000, which is present in an amount of from 2.5 to 15% by weight, based on the total dispersion.

20. The method of claim 19 wherein said thickening agent further comprises a high molecular weight gel forming polymer which is soluble or swellable in water and is capable of forming a matrix together with said particles and said polyalkylene glycol.

21. The method of claim 20 wherein said gel-forming polymer is a synthetic polymer built-up from polycarboxy vinyl chains, polycarboxylalkylene chains, poly-(alkylene oxide) chains or chains of hydroxyalkyl ether on cellulose polymers, said polymers preferably having a molecular weight of at least 400,000 and being present in an amount up to about 4% by weight of said dispersion.

22. The method of claim 14 wherein said thickening agent comprises a gel-forming natural gum which is present in an amount of up to about 5% by weight of the dispersion.

23. The method of claim 14 wherein said dispersion further comprises a low molecular hydrophilic softening agent in an amount up to about 30% by weight.

24. The method of claim 23 wherein the thickening agent is a natural gum and wherein said low molecular hydrophilic softening agent is present in an amount of from 15 to 25% by weight.

25. The method of claim 14 wherein said dispersion is placed in a closed aerosol-type container, said pressure being applied by a liquified propellant and said evacuation of gas being achieved by discharging the same through an orifice provided in the container, by the action of said propellant.

26. The method of claim 14 comprising the steps of evacuating gas from the dispersion, and subjecting the evacuated dispersion to a hydrostatic pressure.

27. The method of claim 2 wherein said particles are cross-linked dextran or cross-linked starch or derivatives thereof.

28. The method of claim 3 wherein said particles are cross-linked dextran or cross-linked starch or derivatives thereof.

29. The method of claim 17 wherein said particles are cross-linked dextran or cross-linked starch or derivatives thereof.

30. The method of claim 18 wherein said particles are cross-linked dextran or cross-linked starch or derivatives thereof.

31. The method of claim 1 wherein the obtained stable preparation is packed in an air-tight container.

32. The method of claim 14 wherein the obtained stable preparation is packed in an air-tight container.

* * * * *